United States Patent [19]

Fiume et al.

[11] Patent Number: 4,794,170

[45] Date of Patent: Dec. 27, 1988

[54] METHOD FOR THE PREPARATION OF CONJUGATES OF ADENINE-9-BETA-ARABINOFURANOSIDE 5' MONOPHOSPHATE WITH LACTOSAMINATED HUMAN ALBUMIN, THE OBTAINED CONJUGATES AND THERAPEUTICALLY ACTIVE COMPOSITIONS CONTAINING THEM

[75] Inventors: Luigi Fiume; Corrado Busi; Alessandro Mattioli, all of Bologna; Massimo Baldacci, Pisa, all of Italy

[73] Assignee: Laboratori Baldacci SpA, Italy

[21] Appl. No.: 807,657

[22] Filed: Dec. 11, 1985

[30] Foreign Application Priority Data

Dec. 11, 1984 [IT] Italy ............................................. 23998

[51] Int. Cl.$^4$ ............................................. C07D 15/06
[52] U.S. Cl. ............................................. 530/363
[58] Field of Search .................... 514/47; 260/121; 530/358, 363

[56] References Cited

PUBLICATIONS

Fuime et al., Febs Lett; 116:185–188 (1980).
Fiume, Febs Letters vol. 129, pp. 261–264, Jul. 1981.
Fiume, Pharmaceutica Acta Helvetiae, No. 11, 1985 (Reprint).

Primary Examiner—Nicky Chan
Attorney, Agent, or Firm—Cushman, Darby & Cushman

[57] ABSTRACT

For the preparation of conjugates of adenine-9-beta-D-arabinofuranoside 5'monophosphate (ara-AMP) with lactosaminated human albumin (L-HSA) aqueous solutions of the two components to be conjugated are brought into contact in the presence of 1-ethyl-3-(dimethylaminopropyl)-carbodiimide, by adjusting the pH in the range from slightly acidic to alkaline and by carrying out the conjugate separation. The resulting conjugate, wherein the molar ratio, as determined through spectrophotometric route, between ara-AMP and L-HSA does vary between 5 and 20, remains soluble after lyophilization even at room temperature and shows biological activity at least equivalent to that of the conjugate as prepared according to the known art.

12 Claims, No Drawings

METHOD FOR THE PREPARATION OF CONJUGATES OF ADENINE-9-BETA-ARABINOFURANOSIDE 5' MONOPHOSPHATE WITH LACTOSAMINATED HUMAN ALBUMIN, THE OBTAINED CONJUGATES AND THERAPEUTICALLY ACTIVE COMPOSITIONS CONTAINING THEM

The present invention relates to conjugates of adenine-9-beta-D-arabinofuranoside 5'monophosphate with lactosaminated human albumin useful in the therapeutical treatment of hepatitis forms of viral origin. Since some years the adenine-9-beta-D-arabinoside (ara-A) and its monophosphate (ara-AMP) are used in the treatment of chronical hepatitis induced by virus B. The ara-A and ara-AMP inhibit the virus replication.

(see: (1) Chadwick R G, Bassendine M F, Crawford E M, Thomas H C, Sherlock S., Br. Med. J., 1978; 2: 531-33.

(2) Pollard R B, Smith J L, Neal E A, Gregory P B, Merigan T L, Robinson W C., JAMA 1978; 239: 1648-50.

(3) Bassendine M F, Chadwick R G, Salmeron J. Shipton U. Thomas H C, Sherlock S., Gastroenterology 1981: 80: 1016-22.

(4) Scullard G H, Pollard R B, Smith J L et al., Infect. Dis 1981; 143: 772-83.

(5) Weller I V D, Bassendine M F, Craxi et al., Gut 1982; 23: 717-23.

(6) Smith C I, Kitchen L K, Scullard G H, Robinson W S, Gregory P B, Merigan T C., JAMA 1982; 247: 2261-65.

(7) Hoofnagle J H, Hanson R G, Minuk G Y et al. Gastroenterology 1984; 86: 150-57).

In some patients these compounds give also place to an improvement of the histological appearance of the liver and a loss of infectivity (see: (8) Scullard G H, Andres L L, Greenberg H B et al. Hepatology 1981; 1: 228-32.

(9) Scullard G H, Greenberg H B, Smith J L, Gregory P B, Merigan T C, Robinson W S, Hepatology 1981; 2: 39-49).

However these drugs cause side effects, mainly at the level of the central nervous system, of the gastrointestinal tract and of the medulla ossium which often cause their administration to be interrupted. These side effects might be eliminated or reduced if the ara-A or the ara-AMP might be selectively carried in the hepatocytes.

see: the already cited paper (7) and (10) Sacks S L, Smith J L, Pollard R B et al. JAMA 1979; 214-28.

(11) Sacks S L; Scullard G H, Pollard R B, Gregory P B, Robinson W S, Merigan T C., Antimicrob. Agents Chemother. 1982; 21-93-100.

(12) Whitley R. Alford C, Hess F, Buchanan R., Drugs 1980; 20-267-82). To this end the ara AMP has been conjugated with lactosaminated albumin (L-SA) which penetrates only in the hepatic parenchima cells wherein it is destroyed by the lysosomes. It has been demonstrated that after administration of the conjugate L-SA-ara-AMP to mice suffering from hepatitis induced by the Ectromelia virus, the ara-AMP is concentrated, in its pharmacologically active form in the hepatocytes. The L-SA-ara-AMP conjugate, when prepared with homologue albumin, is not immunogenic, at least in the mouse.

(see: (13) Fiume L., Busi C., Mattioli A, Balboni P G, Barbanti-Brodano G., FEBS Lett. 1981; 129-261-64.

(14) Ashwell G. Harford J. Annu Rev. Biochem. 1982: 51: 531-54.

(15) Fiume L, Busi C, Mattioli A., FEBS Lett. 1982; 146: 42-46.

(16) Fiume L., Mattioli A, Busi C., Accorsi C., Gut

(17) Fiume L., Mattioli A, Busi C., Spinosa G., Wieland T., Experientia 1982; 38: 1087-89).

The method by which there have been prepared the L-SA-ara-AMP conjugates used in these experiments (18) Fiume L. Mattioli A, Busi C. et al. FEBS Lett; 116: 186-88) is based on this conjugation of activated ara-AMP with L-HSA in acidic environment (pH 5.3-5.5).

This method has the disadvantage of leading to a product which, after the lyophilization, in a short time, (about 1 to 3 days at room temperature and less than one week at 0° to 4° C. as well as some weeks at −20° C.), even if stored at −20° C., becomes insoluble and thus useless for a therapeutical use on wide scale.

The main purpose of the present invention is that of providing a method for the conjugation between ara-AMP and lactosamininated human albumin which gives a conjugate product which remains indefinitely soluble after the lyophilization. This purpose is achieved by means of a conjugation method between ara-AMP and L-SHA which is characterized in that ara-AMP activated with carbodiimide and L-SHA are contacted with each other at a pH higher than 6.5.

According to the preferred embodiment, ara-AMP and L-SHA in form of aqueous solutions are contacted in the presence of carbodiimide, particularly 1-ethyl-3-(dimethyl-aminopropyl)-carbodiimide, whereby the activation of the ara-AMP is carried out directly in the reaction medium. As it will be seen from the following detailed description, the conjugates obtained by the method of the present invention show a molar ratio between ara-AMP and protein, as calculated by spectrophotometric route, varying between 5 and 20. The main advantage of the present invention resides in that, the therapeutical activity being the same, the conjugates of the present invention, after the preparation and the lyophilization, remain soluble and thus therapeutically useful even if stored at room temperature, it meaning that it is possible and made possible and foreseable an industrial production, whereas previously the conjugate had to be used almost immediately after the preparation, owing to the fact that it was becoming insoluble in a short time. This purpose is thus attained by the method according to the present invention as above defined, wherein adenine-9-beta-D-arabinofuranoside 5' monophosphate is conjugated with lactosaminated human albumin, characterized in that the two components to be conjugated in aqueous solution are incubated under stirring in the presence of a carbodiimide, preferably 1-ethyl-3-(dimethyl-aminopropyl)-carbodiimide, and by the reaction mixture pH is adjusted to a value higher than 6.5, the reaction mixture being then separated.

Although the reasons for which with the process of the present invention a conjugate is obtained which remains soluble after lyophilization even if maintained at room temperature have not yet been clarified, it seem plausible to give the following theoretical explanation of such a result. In the conjugation of ara AMP activated with carbodiimide having the formula:

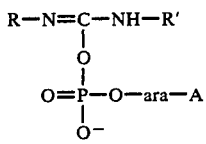

with lactosaminated human albumin, it too activated with carbodiimide, having the formula:

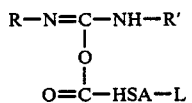

(wherein R and R' represent the specific chemical groups present on the carbodiimide) five derivatives can be formed, namely:

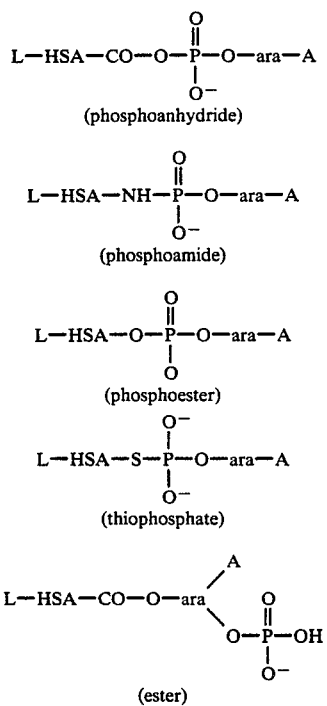

(wherein the type of band being formed is indicated between brackets). The first four derivatives originate from the reaction of ara-AMP activated by the carbodiimide, with the groups COO−, NH₂, OH, SH, of the L-HSA respectively.

The fifth derivative originates from the reaction of the carboxylic groups of the L-HSA (activated by the carbodiimide) with the OH groups of the sugar (arabinose) of the ara-AMP. However the formation of this fifth derivative is not probable since the OH groups of the arabinose, available in the ara-AMP, are secondary OH groups, which can be esterified only under strong conditions.

In the first derivative the phosphate of ara-AMP is bonded to the carboxylic groups of the protein through a phosphoanhydride bond. This is an extremely reactive bond which, in the presence of a NH₂ group undergoes an aminolysis whereby a carboamidic band is formed and the phosphate is released (G. Di Sabato, W. P. Jencks, J. Am. Chem. Soc. 83, 4393–4400, 1961).

In the conjugates prepared at acidic pH the phosphoanhydride bond by reacting after lyophilization with the NH₂ groups of another L-HSA molecule forms a carboamidic bond with the attendant polymerization of the L-HSA molecules. This progressive polymerization is responsible of the solubility loss of the derivatives. By RMN spectroscopic analysis of $^{31}P$ it has been found that in the conjugate prepared at acidic pH, such as 5.5, all the bonds between ara-AMF and L-HSA are of phosphoanhydridic type, whereas when the preparation is carried out at higher pH, for instance 7.5 the bonds between ara-AMP and L-HSA are of two types:

(a) phosphoamidic between the ara-AMP phosphate and the lysine residue epsilon-NH₂ of the protein, (b) phosphoanhydridic between ara-AMP phosphate and the carboxylic residues (glutamic and/or aspartic) of the protein.

The ratio between the two types of bonds is thus seemingly dependent on the pH of conjugation. This is very probably due to the fact that the NH₂ groups of the L-HSA which at acidic pH are fully protonated (—NH₃⁺), and thus cannot react with the ara-AMP as activated by the carbodiimide, at alkaline pH are on the contrary at least partially deprotonated and are thus able to successfully compete with the COO⁻ groups in the reaction with the activated ara-AMP, thus leading to the formation of the second derivative (phosphoanhydride band). This is confirmed by the experiments of Halloran and Parker (J. Immun. 96, 373, 378, 1966) who carried out at pH 7.5 the conjugation of the thymidylic acid with the human albumin by means of carbodiimides and were able to demonstrate that under these conditions only phosphoamidates are formed (same bond as in the present compound 2).

Conjugates of ara-A with lactosaminated albumin can be obtained also through reaction routes different from the above ones, starting from the not phosphorilated nucleoside ara-A can be converted by means of succinic anhydride into ara-A succinate or, by means of glutaric anhydride, into ara-A glutarate. Thereafter these derivatives can be bonded to L-HSA either through their succinimidoester or by the mixed anhydride method or by means of carbodiimides. By means of one of these methods, ara-A was converted into ara-A glutarate which has been then bonded to the asialofetuine (AF) through its hydroxysuccinimidic ester (AF is a glycoprotein which, likewise L-HSA, does not selectively penetrate into the hepatocytes). The ara-A-glut-AF conjugate was thus obtained which was found to be pharmacologically active in producing in the mouse a hepatic targeting of ara-A (Fiume et al., FEBS Lett. 116, 185–188 (1980)).

The following examples illustrate in non limiting was the method of the present invention.

EXAMPLE 1

75 mg (216 μmoles) of ara-AMP are dissolved in 1.5 ml H₂O with the addition of NaHCO₃ (powder). To this solution 75 mg (0.946 μmoles) of L-HSA are added (molar ratio lactose/albumin=29–31). Upon the L-HSA is dissolved the pH is brought to 7.5 with 10N NaOH under potentiometric control and there are added 75 mg (391 μmoles) of 1-ethyl-3-(dimethylaminopropyl)carbodiimide. The mixture is incubated for 24 hours at 25° C. in the dark and under stirring and then, after the addition of two volumes of 0.9% NaCl, is chromatographed on a Sephadex G-100 column (40–120μ) 1.9×130 cm, equilibrated and eluted with a 0.9% solution of NaCl.

The fractions corresponding to the monomer and to the oligomers of L-HSA are combined and dialized at 2°–4° C. against $H_2O$ the pH of which is adjusted to 7.5–8 with $NaHCO_3$. The conjugate is then lyophilized (50–55 mg). The conjugate is soluble in physiological solution (0.9% NaCl) up to 100 mg/ml (maximum tested concentration).

The electrophoresis in polyacrylamide gel has been carried out in the presence of sodium dodecylsulfate, according to the method of Weber K. and Osborn M., J. Biol. Chem. 1969, 244, 4406–12.

After electrophoresis the gel was coloured with Coomassie brilliant blue and the densitometric bond analysis was carried out. The highest rate bond has the mobility of the lactosaminated human albumin; the next bond has the mobility of the 7S γ-globulin of the rabbit. By plotting in a chart the electrophoretic mobility in the abscissae and the logaritm of the molecular weights of L-HSA and of its oligomeric forms (monomer, dimer, trimer and tetramer) in the ordinates a straight line is obtained. This fact does suggest that the second, third and fourth band (in the rate decreasing order) respectively correspond to dimer, trimer and tetramer of L-HSA.

The electrophoresis shows that the conjugate comprises by about 37% the L-HSA monomer, by 22% the dimer, by 15% the trimer, and by 8% the tetramer, whereas the remaining 18% consists of higher oligomers of L-HSA. These percentages do not change in the longrun as demonstrated by the electrophoretical analysis carried out 4 months after the lyophilization. It is thus demonstrated that the conjugate prepared according to the above described method, contrarily to the conjugate prepared according to the known method, does not undergo a polymerization after lyophilization.

In order to measure the molar ratio ara-AMP/protein of the lyophilized conjugate, the latter is again chromatographed on a Sephadex G-100 column, equilibrated and eluted with 0.9% NaCl.

The molar ratio is determined by spectrophotometric route in the following manner. The concetration of the albumin is measured by the method of Lowry et al (J. Biol. Chem. 1951, 193, 266-75) and then the optical density at 260 mμ is read at the spectrophotometer. Then the contribute given at that wave length by the albumin ($E_{1\ cm\ 260} = 3.86$) is subtracted and from the resulting value the concentration of ara-AMP ($E_{1\ cm\ 260} = 420$) is calculated. The molar ratio of six different preparations of the conjugate obtained with the above described method was found to be 13–15. The solubility and the molar ratio ara-AMP/L-HSA of the conjugate, maintained at 0°–4° C. or at room temperature, do not decrease in the long rum (at least up to 4 months, the maximum time tested to date).

EXAMPLE 2

150 mg of ara-AMP are dissolved in 3 ml $H_2$ with the addition of $NaHCO_3$ (powder). To this solution 150 mg of $L_{30}$-HSA are added. Upon the L-HSA is dissolved, the pH is adjusted to 7.5 with 10N NaOH under potentometric control and thereafter 150 mg of 1-ethyl-3-(dimethylaminoproyl)carbodiimide are added. The mixture is incubated for 24 hours at 25° C., in the dark and under stirring.

The mixture (about 3 ml) is dialized in a Visking tube having 6.3 mm dimater placed into a flask containing 5 liters of a 0.3% water solution of NaCl, maintained under stirring by magnetic means.

Under these conditions no precipitation of the conjugate takes place. The dialysis is continued for 24 hours at 0°–4° C. and the 0.3% solution of NaCl is changed two times. After 24 hours and the two said changes no longer free ara-AMP is present.

The conjugate is collected and the volume thereof is measured. The conjugate (150 mg) is now contained in dissolved state in a solution containing NaCl (3 mg/ml). Further NaCl is added so that per each 100 mg of conjugate 9 mg of NaCl are present and then the lyophilization is carried out. In this matter by dissolving 109 mg of the lyophilized preparation with 1 ml $H_2O$ (the solubility being optimum) a solution is obtained of 100 mg of conjugate in 1 ml of physiological solution (0.9% NaCl) ready for the injection or which can be further diluted with physiological solution.

Biological properties of the
ara-AMP-L-HSA-conjugate prepared according to
example 1

The conjugation with ara-AMP does not affect the capacity of L-HSA of interacting with the receptors of the hepatocytes specific for the proteins ending with the galactose.

In fact, (as it appears from the data hereinafter reported) in the mouse the disappearance of the radioactive asialofetuine (AF) from the plasma is competitively inhibited at the same rate by the conjugate and by an equal amount of non conjugated $L_{31}HSA$ (Fetuine is a protein of the bovine phoetal serum which, after removal of the sialic acid, uncovers galactose residues and penetrates selectively into the hepatocytes (see the already mentioned paper of Ashwell et al (14)).

TABELLA 1

| Action of the $L_{31}$-HSA-ara $AMP_{14}$ on the disappearance from plasma of [$^{14}C$]asialofetuine (AF) | |
|---|---|
| Compound injected with [$^{14}C$]AF | dpm/ml of plasma |
| none | 3,795 ± 609 |
| $L_{31}$-HSA | 9,446 ± 1,462 |
| $L_{31}$-HSA-ara-$AMP_{14}$ | 11,275 ± 1,194 |

The fetuine was enzymatically desialated ((22) Morell A G, Van der Hamer C J, Scheinberg I H, Ashwell G. J. Biol. Chem. 1966; 241: 3745–49) and then marked with [$^{14}C$]formaldehyde ((23) Cox R A, Greenwell P. Biochem J. 1980; 186–861-72).

Female Swiss mice of 28–30 g were intravenously administered with 2 μg/g of $^{14}C$ AF (4.9×10$^6$ dmp/mg). The $L_{31}$-HSA or the conjugate werre intravenously administered with $^{14}C$ AF at the dose of 2 μg/g. In all cases the injected volume was 10 μl/g. After 10 minutes the animals were killed and the radioactivity of the plasma was measured. Each value represents the average (±S.E.) of the results obtained from 10 mice.

Table 2 shows the action of two doses of the conjugate injected 2 hours before the radioactive thymidine on the synthesis of viral DNA in the liver and of the cellular DNA in the intestine and in the medulla ossium of mice affected by hepatitis induced by Ectromelia virus. The conjugate inhibits the synthesis of DNA in the liver without causing inhibition in the other two organs. The conjugate, administered by intravenous route to the mice at the dose of 1.33 mg/g of body weight, does not cause any evident sign of toxicity. The curve of the body weight increase and that of the food consumption in the ten days following the injection of this dose of conjugate was equal to that of control mice i.v. administered with physiological solution. The dose of 1.33 mg/g is the maximum dose which has been tested and is 40 to 50 times greater than than used for the treatment of hepatitis induced by Ectromelia virus (see Table 2).

TABLE 2

Effect of the conjugate $L_{31}$-HSA-ara-AMP$_{14}$ on the synthesis of DNA in the liver, intestine and *medulla ossium* of mice infected with Ectromelia virus. The experiment was carried out as described in (13) with the changes reported in (16). The conjugate was injected two hours before the radioactive thymidine. The results were statistically evaluated by means of the t test of Student.

| Injected compound | Administered dose μg/g | Inhibition of the DNA synthesis % | | |
|---|---|---|---|---|
| | | liver | intestine | M. ossium |
| $L_{31}$-HSA-ara-AMP$_{14}$ | 25 | 32(P < 0.01) | 5 | 0 |
| $L_{31}$-HSA-ara-AMP$_{14}$ | 35 | 41(P < 0.01) | 1 | 0 |

Further examples of preparation at pH higher than 6.5 of the conjugates L-HSA-ara-AMP These examples are resumed and desumable from the data reported in the following table 3 (the conjugate the preparation of which has been described in the example 1 corresponds to the conjugate No. 1 of the table). By varying the carbodiimide used, the molar ratio lactose/albumin of the L-HSA, the reaction time and temperature, the reactant concentration and the pH values (provided that they are always greater than 6.5) conjugates are always obtained which remain soluble after lyophilization, even if maintained at room temperature.

2. A process according to claim 1, characterized in that the activation of ara-AMP with carbodiimide is directly carried out in the reaction medium containing ara-AMP and L-HSA wherein the carbodiimide is introduced.

3. A process according to claim 1, characterized in that said carbodiimide is 1-ethyl-3-(dimethyl-aminopropyl)-carbodiimide.

4. A process according to claim 1, characterized in that said pH is of between 7.5 and 9.5.

5. A process according to claim 4, characterized in that said pH is 7.5.

6. A process according to claim 1, characterized in that said reaction is carried out at a temperature of 25° C.

7. A process according to claim 1 wherein the carbodiimide is 1-ethyl-3-(dimethyl-aminopropyl)-carbodiimide or 1-cyclohexyl-3-(2-morpholinyl-(4)-ethyl carbodiimide.

8. A process according to claim 7 wherein the pH is between 7.5 and 9.5.

9. A conjugate prepared by the process of claim 1, characterized in that the molar ratio between adenine-9-beta-D-arabinofuranoside 5'monophosphate and lactosaminated human albumin is between 5 and 20.

10. A conjugate of adenine-9-beta-D-arabinofuranoside 5'-monophosphate prepared by the process of claim 1.

11. A conjugate of adenine-9-beta-D-arabinofuranoside 5'-monophosphate prepared by the process of claim 4.

12. A conjugate of adenine-9-beta-D-arabinofuranoside 5'-monophosphate prepared by the process of claim 7.

TABLE 3

| N. of conjugate | used L-HSA | used carbodiimide | Conjugation Conditions | | | | | Obtained conjugates molar ratio solubility | |
|---|---|---|---|---|---|---|---|---|---|
| | | | Concentrations | | | | | | conjugate stored at |
| | | | ara-AMP μmoles/ml | carbodiimide moles/ml | pH | Temperature °C. | incubation time hours | ara-AMP | 0–4° C. or at room temperature |
| 1 | $L_{31}$-HSA | ECDI* | 144 | 261 | 7.5 | 25° C. | 24 | 14 | yes |
| 2 | $L_{31}$-HSA | ECDI | 288 | 522 | 7.5 | 25° C. | 24 | 20 | yes |
| 3 | $L_{31}$-HSA | ECDI | 72 | 130 | 7.5 | 25° C. | 24 | 10 | yes |
| 4 | $L_{31}$-HSA | ECDI | 144 | 130 | 7.5 | 25° C. | 24 | 11 | yes |
| 5 | $L_{31}$-HSA | MorfoCDI** | 144 | 261 | 7.5 | 25° C. | 24 | 12 | yes |
| 6 | $L_{31}$-HSA | ECDI | 144 | 261 | 5.5 | 25° C. | 24 | 16 | no |
| 7+ | $L_{31}$-HSA | ECDI | 144 | 261 | 6.5 | 25° C. | 24 | 11 | no |
| 8 | $L_{31}$-HSA | ECDI | 144 | 261 | 8.5 | 25° C. | 24 | 10 | yes |
| 9 | $L_{31}$-HSA | ECDI | 144 | 261 | 9.5 | 25° C. | 24 | 5 | yes |
| 10 | $L_{31}$-HSA | ECDI | 144 | 261 | 7.5 | 35° C. | 24 | 9 | yes |
| 11 | $L_{31}$-HSA | ECDI | 144 | 261 | 7.5 | 25° C. | 8 | 11 | yes |
| 12 | $L_{20}$-HSA | ECDI | 144 | 261 | 7.5 | 25° C. | 24 | 11 | yes |
| 13 | $L_{51}$-HSA | ECDI | 144 | 261 | 7.5 | 25° C. | 24 | 12 | yes |

*1-ethyl-3-(dimethylaminopropyl) carbodiimide
**1-cyclohexyl-3-(2-morfolinyl-(4)-ethyl carbodiimide
+Partially precipitates during the conjugation

We claim:

1. In a process for the preparation of a conjugate of adenine-9-beta-D-arabinofuranoside 5' monophosphate (ara-AMP) with lactosaminated human albumin (L-HSA) wherein ara-AMP activated with a carbodiimide and lactosaminated human albumin are reacted with each other, the improvement comprising carrying out the conjugation at a pH higher than 6.5 so as to produce a conjugate product which remains soluble after lyophilization.

* * * * *